(12) United States Patent
Gil et al.

(10) Patent No.: US 6,294,553 B1
(45) Date of Patent: Sep. 25, 2001

(54) METHOD FOR TREATING OCULAR PAIN

(75) Inventors: Daniel W. Gil, Corona Del Mar; Michael E. Stern, Mission Viejo; John E. Donello, Dana Point, all of CA (US)

(73) Assignee: Allergan Sales, Inc., Irvine, CA (US)

( * ) Notice: Subject to any disclaimer, the term of this patent is extended or adjusted under 35 U.S.C. 154(b) by 0 days.

(21) Appl. No.: 09/783,160

(22) Filed: Feb. 14, 2001

Related U.S. Application Data

(60) Provisional application No. 60/182,609, filed on Feb. 15, 2000.

(51) Int. Cl.⁷ ................................................. A61K 31/47
(52) U.S. Cl. ................................................................ 514/314
(58) Field of Search ............................................. 514/314

(56) References Cited

U.S. PATENT DOCUMENTS

| | | | |
|---|---|---|---|
| 6,242,442 | 6/2001 | Dean et al. | 514/222.8 |
| 6,248,741 | 6/2001 | Wheeler et al. | 514/249 |

*Primary Examiner*—Raymond Henley, III
(74) *Attorney, Agent, or Firm*—Robert J. Baran; Martin A. Voet; Carlos A. Fisher

(57) ABSTRACT

The invention relates to the use of brimonidine for treating ocular pain.

11 Claims, 1 Drawing Sheet

MECH.
0.5M NaCl
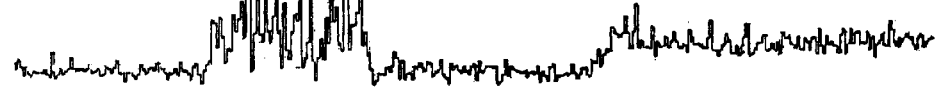
5 MINS.
10 MINS.

METHOD FOR TREATING OCULAR PAIN

CROSS REFERENCE TO RELATED APPLICATIONS

This patent application claims priority from provisional patent application 60/182,609 which was entitled "METHOD FOR TREATING OCULAR PAIN" and was filed on Feb. 15, 2000.

FIELD OF THE INVENTION

This invention relates to the topical application of brimonidine for treating ocular pain and neurogenic inflammation and compositions useful for such application.

BACKGROUND OF THE ART

Pain is a well known phenomenon as an indicator of injury or tissue damage due to inflammation, ischemia, mechanical or other irritation.

The first step leading to the sensation of pain is the activation of nociceptive primary afferents by intense thermal, mechanical or chemical stimuli. Indirect studies of nociceptive transduction (activation) indicate that it involves chemical mediators that are released or synthesized in response to tissue damage. These chemical mediators include lactic acid, hypertonic saline, histamine, 5-hydroxytyptamine, potassium chloride, acetylcholine, purines, bradykinin and substance P which are referred to as algesic agents. In recent years it has been shown that prostaglandins and leukotrienes can contribute to the activation of primary afferent nociceptors. Prostaglandins are uniquely distinguished from the other chemical mediators in that they induce a state of hyperalgesia by elevating the sensitivity of pain receptors to other painful or algesic stimuli.

The stimulation of primary afferents leads to action potentials in their axons which propagate to the spinal cord. In addition, excited primary afferents release neuropeptides (substance P, calcitonin gene-related peptide, neurokinin A) at their peripheral terminals. Neuropeptides enhance inflammatory reactions in the injured tissue, contributing to vasodilation, edema, and increased vascular permeability, this phenomenon is called 'neurogenic inflammation'.

In the spinal cord, the nociceptors enter the gray matter of the superficial dorsal horn to synapse on nerve cells contributing to pain-transmission pathways such as the spinothalamic and spinoreticulothalamic tracts which terminate in two separate regions in the thalamus. The two thalamic regions in turn project to different cortical sites.

The pain transmitting and modulating system depicted so far depends on numerous chemical moieties for its integrated function.

Anesthetics block neuronal transmission and affect sensation as well as pain. Analgesics act by interfering with the activity of chemical mediators of nociception without affecting sensory input.

According to Remington's Pharmaceutical Sciences, 17th Ed., analgesics can be classified as falling into at least three loose groups: 1) the opiate-based (narcotic) analgesics; 2) the non-opiate analgesics; and 3) analgesics and antipyretics.

The opiate-based analgesics include opium derived alkaloids, including morphine, codeine, and their various derivatives, opiate antagonists, the several morphine derivatives which have morphine antagonist activity, but have analgesic activity.

Since these narcotic type drugs are addictive, a number of nonaddictive, non-opiate analgesics have been developed in an attempt to produce an analgesic which is highly efficient but not addictive.

In the third broad category, the analgesics and antipyretics, are the salicylates and acetamide-containing compounds and the so-called non-steroidal anti-inflammatory drugs. They are non-addictive pain killers.

As to their mode of action, drugs that block perception of pain may be said to act either centrally (such as narcotics) or peripherally.

The non-steroidal anti-inflammatory agents (NSAIAs) have been described as peripheral pain relievers. It was further suggested that the analgesic properties of these drugs are independent of their antiedema or anti-inflammatory actions.

The action of NSAIAs as pain relievers is associated with the biosynthesis of prostanoids.

Inflammation or trauma and resultant tissue injuries cause the release of arachidonic acid which is degraded by cyclo-oxygenase and lipoxygenase. The cyclo-oxygenase pathway leads to the synthesis of prostaglandin $E_2$ ($PGE_2$) and other mediators. $PGE_2$ release increases the cyclic AMP and ionic calcium levels at the nociceptor membrane resulting in a lowered activation threshold, resulting in the relay to the central nervous system of augmented pain perception (hyperalgesia). Inhibitors of prostaglandin synthesis, such as NSAIAs, act by avoiding the sensitizing effects of prostaglandins on nociceptive endings and therefore, the decrease in pain threshold.

In animal models and human studies non-steroidal anti-inflammatory agents have been shown to inhibit inflammatory pain.

Ophthalmic applications of various NSAIAs are also known, including the utilization of their anti-inflammatory properties for control of various ocular inflammations.

NSAIAs have been used for the treatment of non-inflammatory, localized pain, such as non-inflammatory ocular pain.

Calcium channel blockers have been suggested as useful for treating pain, including ocular pain.

SUMMARY OF THE INVENTION

As will be appreciated from the above, various peripherally-acting analgesics, anesthetics, etc. have been used to treat ocular pain. However, nowhere is it suggested that the compound utilized in the method of the present invention, i.e. brimonidine that is a centrally-acting analgesic in animal models, may be used to treat ocular pain.

The present invention is based on the unexpected finding that brimonidine efficiently relieves ocular pain, including ocular pain associated with corneal injuries.

The use of a topical composition, including brimonidine, for the relief of eye pain offers several benefits over the use of systemic agents because of the decreased systemic absorption, which may decrease side-effects, and increased ocular absorption that can increase efficacy.

Alpha-2 agonists including brimonidine have been shown to alleviate systemic pain in animal models, including hot plate, tail flick and nerve ligation. One alpha-2 agonist, clonidine, is administered epidurally for treating chronic pain in humans.

The sites of action are presumed to be in the spinal cord and in the brain, where they can reduce the perception of pain. One potential mechanism for the alleviation of pain at the level of the spinal cord is the inhibition of release of the chemical mediators of pain, including substance P and calcitonin gene-related peptide. This mechanism has been demonstrated in vitro for the alpha-2 agonist, dexmedetomidine, acting on rat spinal cord slices (M. Takano, Y. Takano and T. Yaksh, 1993, Release of calcitonin gene-related peptide, substance P, and vasoactive intestinal polypeptide from rat spinal cord: modulation by alpha-2 agonists, Peptides 14, 371–378), and for brimonidine (UK 14304) acting on cultured dorsal root ganglion cells (S. Supowit et al., 1998, Alpha-2 adrenergic receptor activation inhibits calcitonin gene-related peptide expression in cultured dorsal root ganglia neurons, Brain Res. 782, 184–193).

Accordingly, the present invention relates to a method for treating ocular pain in a mammal afflicted by such pain, which method comprises applying to the eye of said mammal an effective amount of brimonidine in a pharmaceutically acceptable vehicle.

BRIEF DESCRIPTION OF THE FIGURE

FIG. 1 shows a recording of the rabbit eye response to 0.5M NaCl, alone, and in the presence of brimonidine.

DETAILED DESCRIPTION OF THE INVENTION

Brimonidine has the structure

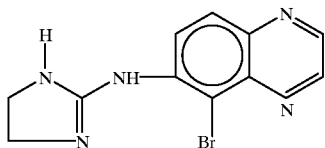

and is also known as 5-bromo-6(2-imidazolin-2-ylamino) quinoxaline. It is available from Allergan, Inc. as the D-tartrate salt and used for treating glaucoma.

An effective dose, when it comes to topical, ocular pain, is a matter of broad therapeutically effective dose requirements. This figure is one controlled by a number of factors: the inherent activity of the drug itself; the vehicle in which it is administered, primarily topical delivery being anticipated; the size of the area to be treated; and the intensity of the pain. Exact dosing data have not been determined but it is anticipated that a topical formulation having between 0.01% and 0.5% (weight/volume) of a brimonidine will provide relief from ocular pain. The determination of the effective dose for any selected compound is well within the skill of an ordinary skilled physician.

In the practice of this invention, brimonidine may be administered in any manner which will deliver the drug directly to the locale of the pain to be treated. It is anticipated that this will be by application to the immediate area of distress. For example, the drug could be applied topically, or by some similar means which delivers the drug directly to the affected area. It is not intended that this invention be practiced by administering the drug in such a way as to insure that it gets to the central nervous system. In fact, that would defeat the whole purpose of this invention which is focused on treating the pain at its source.

For ophthalmic application, preferably solutions are prepared typically containing from about 0.01% to about 0.5% of active ingredient, and a physiological saline solution as a major vehicle. The pH of such ophthalmic solutions should preferably be maintained between 6.5 and 7.2 with an appropriate buffer system. The formulations may also contain conventional, pharmaceutically acceptable preservatives, stabilizers and/or penetration enhancers.

The preferred vehicle that may be used in the ophthalmic solutions of the present invention is purified water, more preferably a physiological saline solution. Additional suitable vehicles include but are not restricted to, viscosity agents such as polyvinyl alcohol, povidone, hydroxypropyl methyl cellulose, poloxamers, carboxymethyl cellulose, carbomer and hydroxyethyl cellulose.

Preferred preservatives that may be used in the ophthalmic formulations of the present invention include, but are not limited to, benzalkonium chloride, chlorobutanol, thimerosal, phenylmercuric acetate and phenylmercuric nitrate.

Penetration enhancers may, for example, be surface active agents; certain organic solvents, such as dimethylsulfoxide and other sulfoxides, dimethylacetamide and pyrrolidone; certain amides of heterocyclic amines, glycols (e.g., propylene glycol); propylene carbonate; oleic acid; alkyl amines and derivatives; various cationic, anionic, nonionic, and amphoteric surface active agents; and the like.

Tonicity adjustors may be added as needed or convenient. They include, but are not limited to, salts, particularly sodium chloride, potassium chloride, mannitol and glycerin, or any other suitable opthalmically acceptable tonicity adjustor.

Various buffers and means for adjusting pH may be used so long as the resulting preparation is ophthalmically acceptable. Accordingly, buffers include acetate buffers, citrate buffers, phosphate buffers and borate buffers for ophthalnic use.

In a similar vein, an ophthalmically acceptable antioxidant for use in the present invention includes, but is not limited to, sodium metabisulfite, sodium thiosulfate, acetylcysteine, butylated hydroxyanisole and butylated hydroxytoluene.

Other excipient components which may be included in the ophthalmic preparations are chelating agents. The preferred chelating agent is edetate disodium, although other chelating agents may also be used in place or in conjunction with it.

The invention is further illustrated by the following non-limiting examples.

EXAMPLE 1

A clinical study is performed to compare the analgesic effect of topically administered brimonidine and placebo following radial keratotomy surgery. One hundred and twenty-four male and female subjects, 21 to 45 years of age, undergo routine, elective, unilateral radial keratotomy for the correction of myopia and brimonidine is administered as a 0.03% ophthalmic solution.

Each subject receives one drop of the assigned study medication every four hours while awake one day prior to surgery and again every 20 minutes for the two hours just before surgery. Each subject then undergoes unilateral radial keratotomy. Following surgery, each subject receives one drop of the study medication in the operated eye every four hours while awake for 14 consecutive days. Postoperative examinations occur at days 1, 3, 7 and 14.

Efficacy is assessed by evaluation of pain intensity, pain relief, subjective global analgesic efficacy. Symptoms of ocular inflammation (burning/stinging, tearing, etc.) are also recorded.

The results of this study show greater pain relief at hours 2, 3 and 4 in the brimonidine group over the group treated with placebo. This appears to suggest that brimonidine, administered preoperatively, blocks the perception of pain.

EXAMPLE 2

A 54 year old woman, hard contact lens wearer, has a one day history of sharp shooting pain in both eyes. Brimonidine is prescribed as a sole treatment of pain. On instillation of the medication, the patient reports relief of pain for approximately two and a half hours. Upon recurrence of pain, a second dose of brimonidine provides pain relief.

EXAMPLE 3

A 32 year old female patient with a history of gas-permeable contact lens wear has a two-to-three day history of pain in her left eye. The patient is treated with brimonidine for pain. The patient reports relief of pain for two hours.

EXAMPLE 4

The effect of brimonidine on ocular pain is also studied using the Corneal Nerve Conduction Model. This model is performed in rabbits as a way to determine the types and quantity of nerve traffic generated as the cornea is exposed to various stimuli. In this model, a rabbit under deep anesthesia is placed in a stereotaxic apparatus. The retro-orbital space is surgically exposed and a hook electrode is placed around the ciliary nerve that sits adjacent to the optic nerve. The ocular surface is fitted with a chamber through the use of a conjunctival pharyngeal ring into which test formulations can be added.

A dose range of an ophthalnic formulation of brimonidine (0.01% to 0.5% for instance) as well as a vehicle is filled into the chamber and the resultant nerve traffic from the cornea is recorded. In this way the effects of brimonidine on ocular surface sensation is determined. This study is also performed in the presence of an ocular surface sensory challenge such as topical capsaicin, potassium chloride or fine hairs.

Ocular responses characteristic of neurogenic inflammation, including redness and pupillary constriction, are also observed in rabbits following external stimuli. The ability of an ophthalmic solution of brimonidine at concentrations ranging from 0.01% to 0.5% to reduce the neurogenic response at 5, 10, 15, 30 and 60 minutes following administration is determined. Brimonidine is effective in reducing such neurogenic responses.

EXAMPLE 5

It has been found that the rabbit neurophysiological model is a predictor of actions on the corneal nerves that are associated with the sensation of corneal irritation and pain in humans. Thus, this experiment is carried out in the anesthetized rabbit and enables one to make decisions as to the effect on the human eye. By comparison with the human psychophysical studies it has been determined when the corneal nerves are activated in the rabbit model-pain would be sensed in the human. When the amount of neural activity is decreased the amount of pain or sensory irritation in the human would decrease. In the rabbit neurophysiological model, one records from the primary sensory axons so the results reflect what is occurring at the sensory receptor in the corneal epithelium.

The FIGURE shows a response at the top, a control response to mechanical stimulation, this is carried out to ensure that the preparation is lively. Test solutions are put into a chamber, about 1 cc, over the surface of the cornea. The test solution is blocked from reaching the axons where the recording is made. Application of a standard stimulus, 0.5M NaCl for 30 seconds elicits rapid action potential activity which lasts beyond the end of the stimulus. The NaCl is washed away by several applications of saline. Brimonidine, as Allergan, Inc.'s Alphagan® pharmaceutical composition, was put into the chamber for 1 minute, and not washed before retesting with the 0.5M NaCl. This was repeated at several intervals and resulted in a decrease in the response for the 0.5M NaCI. Overall, three runs were made and the response decreased by about 35% at 5 mins and then continued to decrease at 10 mins by about 50%. The interpretation of this result is that the sensory response to the human cornea would be decreased. At 60 mins it was found that the response to 0.5M NaCl had returned to about that of the pretest solution. In each record, the top part indicates the raw data and the bottom record the integrated response. Also, at the beginning of each record there is a response to mechanical stimulation. Brimonidine does not alter that response to any real extent. It is commonly found that the chemical thermal response is more labile to drug application. At the same time, preservation of the mechanical response is important for the health of the cornea. In contrast, a topical anesthetic would rapidly decrease the response to mechanical and chemical modalities.

While further experiments would be desirable to validate these results, these results are indicative that brimonidine may be useful to decrease corneal sensory irritation and pain.

The foregoing description details specific formulations and methods that can be employed to practice the present invention. Having detailed specific compositions for the topical formulations of the present invention and specific instructions for their use in the treatment of ocular pain, the art skilled will well enough know how to devise other formulations and how to adapt the treatment (formulations, doses) to a special situation. Thus, however detailed the foregoing may appear in text, it should not be construed as limiting the overall scope hereof; rather, the ambit of the present invention is to be governed only by the lawful construction of the appended claims.

What is claimed is:

1. A method for alleviating ocular surface pain in a mammalian eye comprising administering to a mammalian eye having ocular surface pain an amount of brimonidine effective to alleviate the ocular surface pain.

2. The method of claim 1 wherein said mammalian eye is a human eye.

3. The method of claim 1 wherein said administration is topical administration directly to said eye.

4. The method of claim 1 wherein said brimonidine is administered in solution in a pharmaceutically acceptable ophthalmic vehicle.

5. The method of claim 1 wherein said effective amount is from about 0.005 to about 1 mg per eye per day.

6. The method of claim 4 wherein said vehicle contains from about 0.05 to about 5 mg per ml of said brimonidine.

7. The method of claim 1 wherein said pain is associated with a wound or inflammation in said eye.

8. The method of claim 1 wherein said pain is associated with radial keratotomy.

9. The method of claim 1 wherein said pain is associated with treatment by a laser.

10. The method of claim 9 wherein said laser is an excimer laser.

11. The method of claim 1 wherein said pain is associated with corneal abrasion.

* * * * *